United States Patent
Schmitt et al.

(10) Patent No.: US 10,426,446 B2
(45) Date of Patent: Oct. 1, 2019

(54) STRAW FOR THE PRESERVATION OF A PREDETERMINED DOSE OF LIQUID-BASED SUBSTANCE, IN PARTICULAR PURE OR DILUTED ANIMAL SEMEN; AND SET COMPRISING IT

(71) Applicant: IMV TECHNOLOGIES, Saint Ouen sur Iton (FR)

(72) Inventors: Eric Schmitt, Villaines-la-Juhel (FR); Olivier Carion, Rai (FR); Jean-Charles Gorges, Chenay (FR)

(73) Assignee: IMV TECHNOLOGIES, Saint Ouen Sur Iton (FR)

( * ) Notice: Subject to any disclaimer, the term of this patent is extended or adjusted under 35 U.S.C. 154(b) by 493 days.

(21) Appl. No.: 15/029,752

(22) PCT Filed: Oct. 13, 2014

(86) PCT No.: PCT/FR2014/052597
§ 371 (c)(1),
(2) Date: Apr. 15, 2016

(87) PCT Pub. No.: WO2015/055929
PCT Pub. Date: Apr. 23, 2015

(65) Prior Publication Data
US 2016/0228101 A1  Aug. 11, 2016

(30) Foreign Application Priority Data

Oct. 15, 2013  (FR) ...................................... 13 60036

(51) Int. Cl.
*A61B 10/00* (2006.01)
*A61D 19/02* (2006.01)
*A01N 1/02* (2006.01)

(52) U.S. Cl.
CPC ........ *A61B 10/0058* (2013.01); *A01N 1/0263* (2013.01); *A61D 19/024* (2013.01); *A61B 2562/08* (2013.01)

(58) Field of Classification Search
CPC ...... A61D 19/00; A61D 19/02; A61D 19/022; A61D 19/024; A01N 1/0263; A01N 1/0268; A61B 17/42; A61B 17/425; A61B 17/435

See application file for complete search history.

(56) References Cited

U.S. PATENT DOCUMENTS

| 4,134,359 A | 1/1979 | Redpath |
| 5,851,491 A | 12/1998 | Moulton |
| 5,868,178 A * | 2/1999 | Lecointe ............... A61D 19/024 119/174 |
| 5,912,115 A * | 6/1999 | Hyman .................... C12Q 1/04 422/50 |
| 6,369,894 B1 * | 4/2002 | Rasimas ............... G01N 21/645 250/458.1 |
| 7,056,727 B2 | 6/2006 | Saint-Ramon et al. |
| 7,252,988 B2 | 8/2007 | Saint-Ramon et al. |
| 2002/0188222 A1* | 12/2002 | Saint-Ramon ....... A61D 19/024 600/573 |
| 2006/0177352 A1 | 8/2006 | Ziegmann et al. |
| 2008/0199363 A1 | 8/2008 | Mao |
| 2011/0195446 A1 | 8/2011 | Lee et al. |
| 2012/0264207 A1 | 10/2012 | Sharpe et al. |

FOREIGN PATENT DOCUMENTS

| EP | 0873726 A1 | 10/1998 |
| FR | 995878 A | 12/1951 |
| FR | 2824255 A1 | 11/2002 |
| FR | 2824256 A1 | 11/2002 |
| GB | 669265 A | 4/1952 |
| KR | 100941323 B1 | 2/2010 |
| WO | 2010070533 A1 | 6/2010 |

* cited by examiner

*Primary Examiner* — Carrie R Dorna
(74) *Attorney, Agent, or Firm* — Browdy and Neimark, P.L.L.C.

(57) ABSTRACT

The container straw comprises a tube (11) and a stopper (12) that is permeable to gasses and impermeable to liquids, which stopper (12) is arranged in the tube (11) near one end (16), characterized in that it comprises an indicator component (20) configured to emit, at least when the container straw (10) is full, light the spectrum of which contains at least one spike having a peak of predetermined wavelength. The assembly comprises the container straw (10) and a container straw recognition device (26).

14 Claims, 2 Drawing Sheets

STRAW FOR THE PRESERVATION OF A PREDETERMINED DOSE OF LIQUID-BASED SUBSTANCE, IN PARTICULAR PURE OR DILUTED ANIMAL SEMEN; AND SET COMPRISING IT

The invention generally relates to the preservation of a predetermined dose of liquid-based substance, in particular pure or diluted animal semen; and more particularly to the straws for performing such preservation.

It is known that such a straw comprises a tube and a stopper disposed in the tube. The stopper is usually of the three-part type originally described in French patent 995 878, corresponding to British patent 669 265, i.e. formed by two plugs made from a fibrous substance enclosing a powder which, on contact with a liquid, transforms into an impermeable paste or gel adhering to the wall of the tube so that the stopper is liquid-tight.

Similar but improved stoppers are described by the French patent applications 2 824 255 and 2 824 256.

Stoppers of another type are also known, for example a stopper made from a single-piece cylinder of hydrophobic microporous material described by European patent application 0 873 726 or a stopper made from a single-piece cylinder of sintered self-sealing microporous material as described by PCT application WO 2010/070533.

In the initial state, the stopper is disposed in the neighborhood of one of the ends of the tube and it is provided that in the filled state, the dose of liquid substance which must be preserved in the straw is disposed between the stopper and the other end of the tube (the end furthest from the stopper). The tube and the stopper are configured for the stopper to be able to slide in the tube towards the end that is initially furthest from the stopper.

To fill the straw, the end closest to the stopper is placed in communication with a vacuum source while the furthest end of the tube is placed in communication with a vessel containing the substance to be introduced into the straw.

The air initially contained between the stopper and the furthest end of the tube is sucked through the stopper while the substance moves forward into the tube until it meets the stopper.

If necessary, after filling, the straw is welded close to one or both of its ends and is stored cold.

In order to empty the straw, if necessary after cutting the welded end portions and thawing, a rod is inserted into the tube via the end closest to the stopper, until it bears against the stopper. Using this rod, the plug is made to slide in the manner of a piston towards the end furthest from the stopper, which causes the expulsion of the dose of substance which had been introduced into the straw.

The invention aims to provide such a straw capable of being discriminated from other straws.

To that end the invention provides a straw for the preservation of a predetermined dose of liquid-based substance, comprising a tube and a gas-permeable liquid-tight stopper, which stopper is disposed in the tube in the neighborhood of one end, characterized in that it comprises an indicator component configured to emit, at least when the straw is in the filled state, light of which the spectrum comprises at least one peak having a crest of predetermined wavelength.

In contrast, a conventional straw emits light of which the light of which the spectrum is relatively uniform.

The detection of the presence in or of the absence from the light emitted by the indicator component, of the peak or peaks having a crest of predetermined wavelength makes it possible to recognize whether the current straw is an ordinary straw or a straw provided to be discriminated.

Such determination is particularly simple to perform, visually by an operator or automatically.

The implementation of the straw according to the invention and of the detection of the proper filling thereof is furthermore feasible in a particularly simple and economical manner, in particular as set out below.

According to advantageous features:
- said indicator component is configured to emit light of which the spectrum comprises several said peaks of which the crests are of different wavelengths;
- said indicator component is configured to emit light of which the spectrum comprises said at least one peak in response to illumination by light comprising a predetermined range of wavelengths that is offset relative to the predetermined wavelength of said crest;
- said indicator component forms part of said stopper and is configured to emit light comprising said at least one peak when it has been in contact with said substance and does not comprise said at least one peak in the absence of prior contact with said substance;
- said stopper is formed by two plugs made from a fibrous substance enclosing a sealing agent formed by a powder transforming on contact with said substance into an impermeable paste or gel adhering to the wall of the tube so that the stopper is liquid-tight, said indicator component comprising said sealing agent;
- said powder comprises a powder of a salt that is non-fluorophore in the dry state and fluorophore when it is dissolved in water;
- said salt forms part of the group comprising a fluorescein salt, a Rhodamine B salt, a Rhodamine 6G salt and a salt of ERIOCHROME® Cyanine R;
- said powder comprises between 1/100 and 1/100000 by weight of said salt powder;
- said powder is formed by said salt powder and by powder of material that polymerizes on contact with water;
- said powder of material that polymerizes on contact with water is alginate;
- said indicator component comprises an indicator thread configured to emit said light of which the spectrum comprises said at least one peak; and/or
- said stopper is formed by two plugs made from a braided fibrous substance enclosing a sealing agent formed by a powder which, on contact with a liquid, transforms into an impermeable paste or gel adhering to the wall of the tube so that the stopper is liquid-tight, at least one of the two plugs comprising said indicator thread.

The invention is also is directed to a set comprising a straw as set forth above and a device for recognition of said straw, characterized in that said recognition device comprises a detection member for detecting the absence or the presence of said at least one peak in the light spectrum emitted by said indicator component.

According to advantageous features:
- said indicator component of the stopper of the straw is configured to emit light of which the spectrum comprises said at least one peak in response to illumination by light comprising a predetermined range of wavelengths that is offset relative to the predetermined wavelength of said crest; and said recognition device further comprises an illuminating member to illuminate said indicator component by light comprising said predetermined range of wavelengths; and/or
- said recognition device is configured to detect the absence or the presence of each said peak.

The disclosure of the invention will now be continued with the description of embodiments, given below given below by way of non-limiting example, with reference to the attached drawings, in which.

Figure 1:
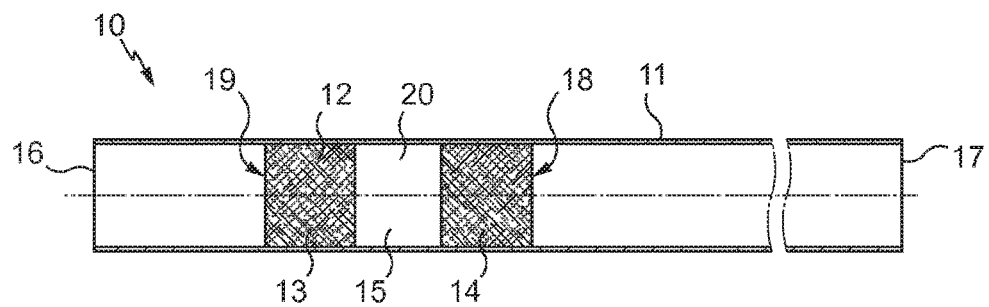
FIG. 1 is a diagrammatic view in longitudinal section of a straw according to the invention, in the empty state.

The straw 10 illustrated in FIG. 1 comprises a tube 11 and a stopper 12.

The tube 11 is conventionally made from extruded plastic material, here transparent, with an inside diameter for example of 1.6 or 2.5 mm and a length of the order of 133 mm.

The stopper 12 is of the three-part type, i.e. formed by two plugs 13 and 14 made from a fibrous substance enclosing a sealing agent 20 formed by a powder (FIG. 1) which, on contact with a liquid, is capable of transforming into an impermeable paste or gel 15' (FIG. 2) adhering to the wall of the tube 11 so that the stopper 12 is liquid-tight.

In the initial state, shown in FIG. 1, the stopper 12 is disposed in the neighborhood of the end 16 of the tube 11 and it is provided that in the filled state, the dose of liquid-based substance which must be preserved in the straw 10 is disposed between the stopper 12 and the end 17 of the tube 11 that is the furthest from the stopper 12.

In order to fill the straw 10, the end 16 is placed in communication with a vacuum source while the end 17 is placed in communication with a vessel containing the substance to be introduced into the straw.

Figure 2:
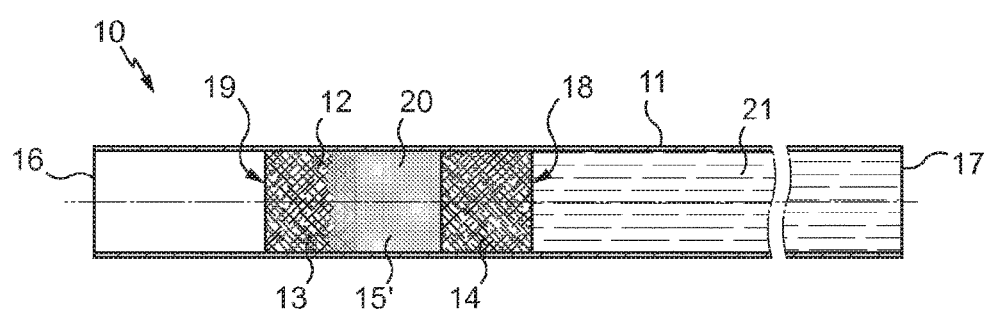
FIG. 2 is a view similar to FIG. 1 but showing the straw in the filled state.

The air initially contained between the stopper 12 and the end 17 is sucked through the stopper 12 while the substance 21 (FIG. 2) moves forward in the tube 11 until it encounters the stopper 12, by the end 18 thereof that is turned towards the end 17 of the tube 11, that is to say the end of the stopper 12 that can be seen on the right in FIGS. 1 and 2.

The straw 10 is then in the filled state shown in FIG. 2.

If necessary, after filling, the straw is welded in the neighborhood of one or both of its ends 16 and 17 and is placed in cold storage.

To empty the straw 10, if necessary after cutting the welded end portions and thawing, there is inserted into the tube 11 a rod which comes to bear on the end 19 of the stopper 12 (which end is situated on the opposite side to the end 18).

Using this rod, the stopper 12 is made to slide in the manner of a piston towards the end 17 or the end which corresponds after cutting the welded portion, which causes the expulsion of the dose of substance 21 which had been introduced into the straw.

On comparing FIGS. 1 and 2, it will be noted that the stopper 12 has a different aspect when the straw 10 is in the empty state (FIG. 1) and the filled state (FIG. 2).

When the straw 10 is in the empty state, the sealing agent 20 (powder 15) of the stopper 12 is of a first color and when the straw 10 is in the filled state, the sealing agent 20 (gel 15') is of a second color.

Here, the hue of the first color (empty state) is brownish white while the hue of the second color (filled state) is greenish yellow.

For example, the powder 15, as seen through tube 11, is of Pantone® 155U color and the gel 15', as seen through the tube 11, is of Pantone® 395C color.

It is recalled here that the hue of a color corresponds to the wavelengths (or to the single wavelength in the case of a color of the rainbow) of the light emitted by the object having that color. The hue is only one of the components of the color, which depends on other parameters such as luminosity and saturation.

The change in hue between the powder 15 and the gel 15' is due to the presence, in the sealing agent 20, of a product changing hue between the dry state and the state dissolved in water.

Here, the product changing color is the sodium salt of fluorescein.

It will be noted that the fluorescein sodium salt is not spermicidal and therefore is suitable for contact with animal semen.

It is known that the fluorescein sodium salt has the following formula:

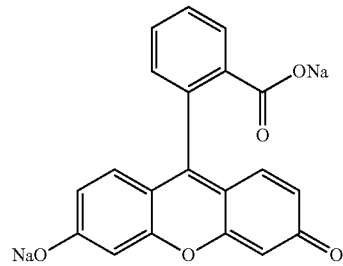

and that it is identified by the number CAS 518-47-8.

It is also known that the fluorescein sodium salt is a fluorophore salt i.e. capable of emitting fluorescent light when it is dissolved in water; while in the dry state it is a non-fluorophore salt.

When the sealing agent 20 of the stopper 12 is in the dry state (powder 15) the fluorescein sodium salt does not emit fluorescent light since it is in the dry state. When the sealing agent 20 of the stopper 12 is in the dampened state (gel 15'), the fluorescein sodium salt is dissolved in the water contained in the gel 15' and then emits fluorescent light.

The change in hue of the sealing agent 20 is due to the addition of fluorescent light.

By virtue of the presence of the fluorescein sodium salt, the sealing agent 20 forms an indicator component indicating contact between the stopper 12 and the substance 21: the sealing agent 20 is of a predetermined color in the absence of prior contact with the substance 21 and a second predetermined color, having a different hue to the hue of the first color, when the sealing agent 20 has been in contact with the substance 21.

It will be observed, as illustrated in FIG. 2, that in the dampened state of the stopper 12, part of the plug 13 has taken on the same hue as the gel 15'.

As a matter of fact, on filling the straw, between the moment when the substance 21 reached the powder 15 and the moment when the powder 15 transformed into a liquid-tight gel 15', a small quantity of powder 15 dissolved by the substance 21 but not yet gelled was absorbed by the plug 13.

The indicator component indicating contact with the substance 21, formed by the sealing agent, is useful for checking the proper filling of the straw 10, and more precisely the proper dampening of the stopper 12 by the substance 21.

It is known that it is very important, for the proper preservation of the substance 21 contained in the straw 10, that the stopper 12 be correctly dampened. As a matter of fact, in a case in which the straw 10 is not welded at its ends, or welded only at the end 17 furthest from the stopper 12, the fluid-tightness of the straw 10 is ensured in part by the stopper 12.

On emptying the straw 10, the correct dampening of the stopper 12 on filling enables the stopper 12 to play its piston role without there being leaks between the tube 11 and the stopper 12.

Checking the proper filling of the straw can be carried out visually by the operator, simply by verifying that the sealing agent 20 of the stopper 12 has indeed adopted the hue of the second predetermined color, i.e. a greenish yellow hue in the present example.

The proper filling of the straw 10 can also be checked automatically, as will be explained below.

Figure 3:
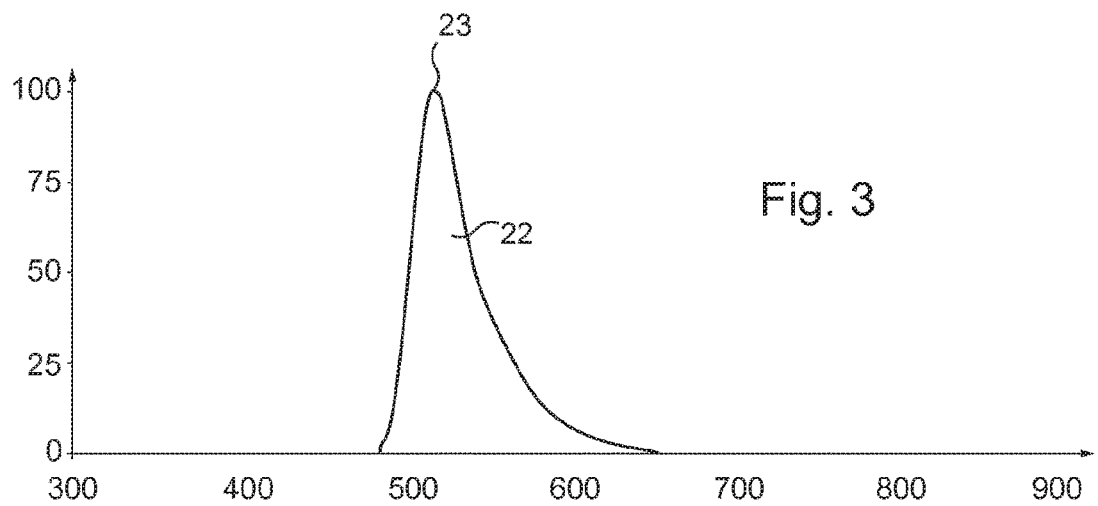
FIG. 3 is a graph illustrating the spectrum of the light emitted by a fluorophore agent comprised by the stopper of the plug when the straw is in the filled state.

FIG. 3 is a graph illustrating the spectrum of the light emitted by the fluorescein sodium salt when it is dissolved in water, i.e. the fluorophore agent contained by the gel 15'. In the graph of FIG. 3, the wavelengths in nm are along the abscissa axis and the relative intensity of the emission is along the ordinate axis.

It can be seen that the fluorescein sodium salt in the state dissolved in water emits light of which the spectrum comprises a peak 22 having a crest 23 the wavelength of which is of the order of 520 nm, which corresponds to the aforementioned greenish yellow hue; and that the peak is relatively narrow, which it typical of light from fluorescence.

The light emitted by the sealing agent 20 in the dampened state (gel 15') has a broader spectrum but also comprises a peak 22 having a crest 23.

In the spectrum, the apex of the peak 22 situated in the neighborhood of the crest 23 is clearly distinct from the rest of the spectrum and may thus be relatively easily identified by an automatic device.

Figure 4:
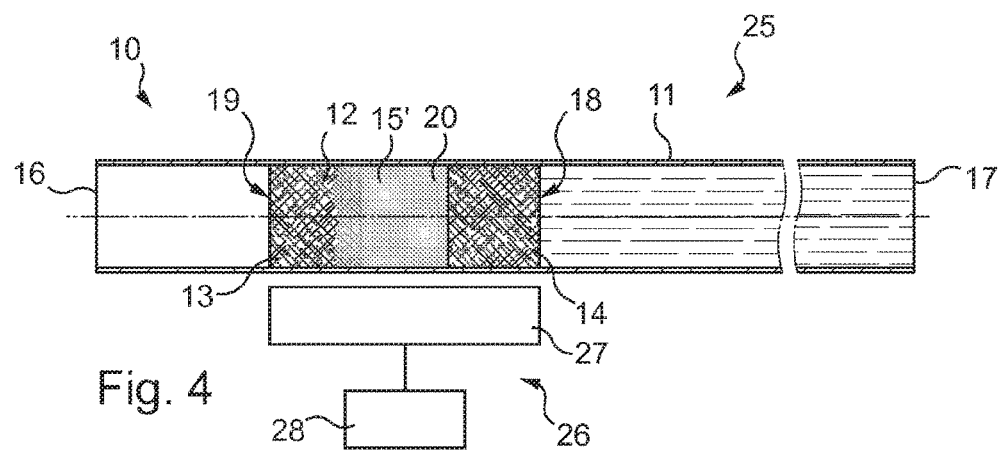
FIG. 4 is a similar view to FIG. 2 but showing the straw in a machine comprising a device for recognizing the straw.

FIG. 4 shows a machine 25 for filling straws comprising a device 26 for checking filling of the straws 10 filled by the machine 25.

The checking device 26 comprises a member 27 for detecting whether the indicator component 20 has taken on the hue of the second color, that is to say the hue of the gel 15'.

Here, the detection member 27 comprises an electronic photoreceptor member and a member for electronic analysis of the information provided by the photoreceptor member to determine whether the spectrum of the light received by the photoreceptor member comprises the apex of the peak 22 situated in the neighborhood of the crest 23.

In addition to the detection member 27, the checking device 26 comprises a processing unit 28 linked to the detection member 27 and configured to emit a stop signal for the filling machine 25 in case the detection member 27 detects a straw 10 in which the indicator component 20 has not taken on the hue of the second color.

When the stop signal is emitted, the filling machine 25 stops.

An operator may then identify the reasons for the improper filling of the straw and solve the problem which may have occurred.

It will be noted that in the dry state, the fluorescein sodium salt is hydrophilic. It thus dissolves practically instantaneously in contact with the liquid-based substance 21 which comprises a high proportion of water. Therefore, the reaction time of the indicator component indicating contact formed by the sealing agent 20 is particularly brief.

By virtue of this high reaction speed, the filling device 26 may be disposed in the machine 25 at a filler station and practically instantaneously detect a filling defect of the straw.

By stopping the filler machine, the number of mis-filled straws is minimized, which is very important since in general the substance to preserve in a straw has a high economic value.

The fast reaction time enables the checking of the filling to be implemented including in machines with a high operating rate, capable of filling up to several thousand straws per hour.

The device for checking filling 26 shown in FIG. 4 is capable of operating in ambient light.

Figure 5:
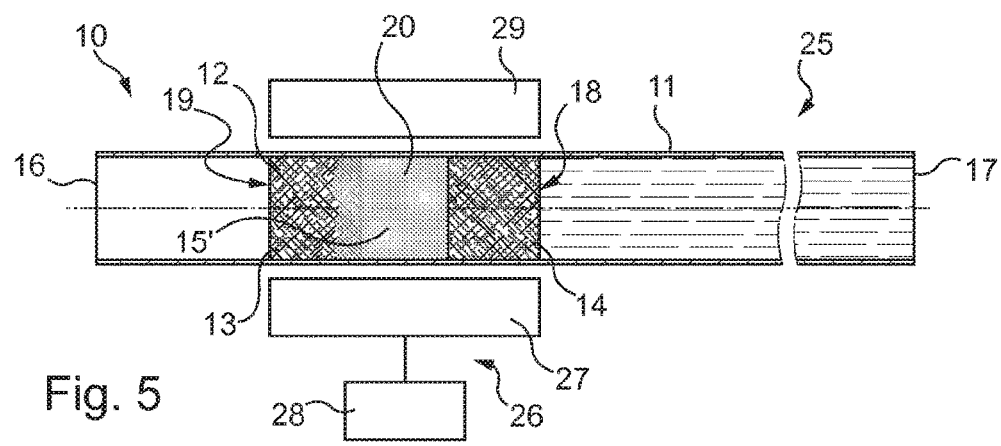
FIG. 5 is a view similar to FIG. 4 but showing a variant of the device for recognizing the straw.

In the variant shown in FIG. 5, which is useful in particular in the situations in which the ambient light is insufficient, the checking device 26 further comprises a lighting member 29 for the sealing agent 20.

It is known that fluorescein sodium salt in the dissolved state in water is mainly excited by a set of wavelengths situated in the neighborhood of 495 nm, i.e. in a predetermined range of wavelengths that is offset relative to the wavelength of the crest 23 (520 nm).

The lighting member 29 emits light comprising that predetermined range of wavelengths.

It is advantageous, so as to avoid the lighting member 29 perturbing the detection member 27, to configure the lighting member 29, by taking advantage of the offset between the excitation wavelength and the emission wavelength so as not to emit light or in any event a minimum of light in the emission range of wavelengths.

In the example illustrated of the stopper 12, the powder 15 comprises 1/1000 by weight of fluorescein sodium salt powder in the dry state.

A range suitable for the implementation of the invention is from 1/100 to 1/100000 by weight of fluorescein sodium salt powder in the dry state.

Advantageously, the range is from 1/500 to 1/50000, and still more advantageously from 1/1000 to 1/25000.

To obtain good homogeneity, the powder 15 is prepared by successive mixing operations.

In the illustrated example of the stopper 12, the powder 15 is exclusively formed by fluorescein sodium salt powder in the dry state and by powder of material that polymerizes on contact with water.

Here, the powder of material that polymerizes on contact with water is alginate.

In a variant of the sealing agent 20, the fluorescein sodium salt powder in the dry state is replaced by another product that is not fluorophore in the dry state and is fluorophore when it is dissolved in water, which is in the form of a salt in the dry state.

This is for example another fluorescein salt, a Rhodamine B salt, a Rhodamine 6G salt and/or a salt of ERIOCHROME® Cyanine R It is known that Rhodamine B has the following formula:

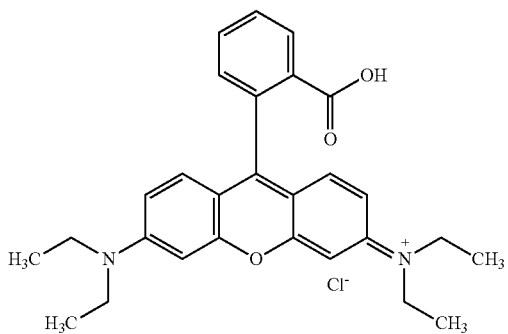

and that it is identified by the number CAS 81-88-9.

It is known that Rhodamine 6G has the following formula:

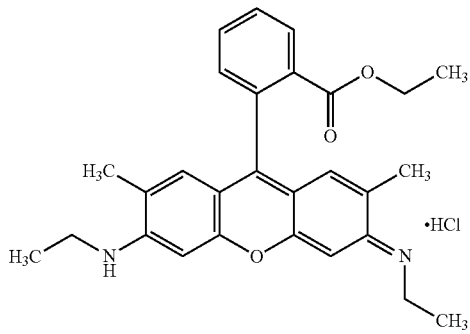 [SMILES: CC/N=c1\cc2oc3cc(NCC)c(C)cc3c(-c3ccccc3C(=O)OCC)c-2cc1C ; Cl]

and that it is identified by the number CAS 989-38-8.

It is known that ERIOCHROME® Cyanine R has the following formula:

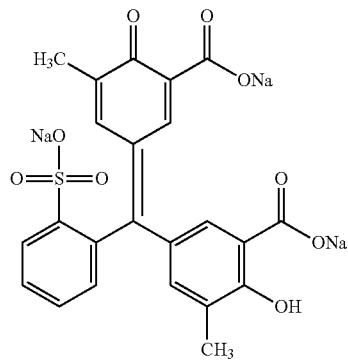

and that it is identified by the number CAS 64-18-9.

Figure 6:
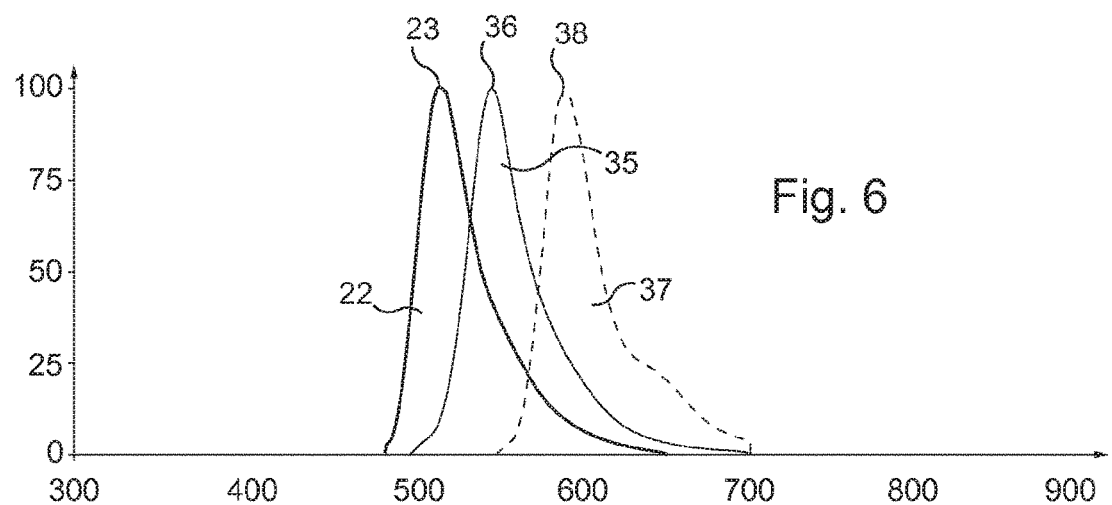
FIG. 6 is a similar view to FIG. 3 but for a variant of the fluorophore agent.

FIG. 6 shows in the same way as FIG. 3 the light spectrum emitted by a mixture of fluorescein, Rhodamine 6G and Rhodamine B.

This spectrum comprises a peak 35 having a crest 36 for Rhodamine 6G and a peak 37 having a crest 38 for Rhodamine B.

It can be seen that the crest 36 has a wavelength of the order of 553 nm and that the crest 38 has a wavelength of the order of 579 nm.

The fluorophore agent comprised by the sealing agent 20 in the dampened state (gel 15') may be formed, as illustrated in FIG. 6, by a mixture of fluorescein, Rhodamine 6G and Rhodamine B or by only one or by two of these products.

By selecting one or more of these products, the hue of the sealing agent 20 in the dampened state (gel 15') can be adjusted. The selection of the hue of the indicator component constituted by the sealing agent 20 when it has been in contact with the substance, enables the straw 10 to be recognized, visually or by analysis of the light spectrum emitted, in particular based on the location of the crest or crests such as 23, 36 and 38, chosen so as not to be superposed.

The detection of the presence or of the absence of each of the crests 23, 36 and 38 enables a particularly advanced recognition of the straw to be made.

It will be noted that by choosing different mixtures, it is possible to have available a range of straws each having an identifier component configured to emit light of which the spectrum comprises a unique combination of light peaks each having a predetermined location, such that the recognition device 26 can also serve for the recognition of a certain type of straw within a range of straws.

Such a recognition capacity is particularly useful, for example to make sure of the origin of the straw or to make sure that it is of a suitable nature to preserve the semen that is being filled by the machine.

In variants not illustrated, the device 27 does not serve for the verification of the proper filling of the straw 10 but only to perform recognition of the straws, in a filler machine or in a location other than a filler machine.

In variants not illustrated, the indicator component comprises, in addition to the fluorophore agent or agents, a coloring agent.

It is known that a coloring agent, contrary to a fluorophore agent, does not emit light comprising a peak having a crest of predetermined wavelength, but a relatively broad range of wavelengths of the same intensity.

The combination of the spectrum of a fluorophore agent and of a coloring agent may be useful for the quality of recognition of the origin of the straw.

The coloring agent, without being a fluorophore, is for example methylene blue or α-zurine.

Such coloring products, when in the dry state, for example in the form of a small proportion of the sealing agent 20 in the dry state (powder 15) do not affect or affect only a very little the color of the other products forming the indicator component, for example the alginate powder. On the other hand, when the indicator component is dampened, the coloring product communicates its coloration to the rest of the indicator component, for example the gel 15'.

In variants not illustrated, the indicator component is different from the sealing agent 20, for example an indicator thread having, just like the sealing agent 20, the capacity of emitting light of which the spectrum comprises at least one peak having a crest of predetermined wavelength. Such an indicator thread is associated with the stopper 12 or with a stopper of different type, for example a stopper made from a single piece cylinder as described in European patent application 0 873 726 or in PCT application WO 2010/070533.

The association of an indicator thread with the stopper 12 is made for example, in the case in which the plug 13 or the plug 14 is a braid made from threads of fibrous substance, by incorporating the thread in the braid. For example, the indicator thread is braided with the threads of fibrous substance.

It is also possible to associate several indicator threads with the stopper 12.

For example, the indicator thread or threads are disposed in the center of the buffer 14 and communicate their coloration to the rest of the plug 14 when it is dampened.

In another variant, the indicator component is formed both by the sealing agent 20 and by the indicator thread associated with the stopper 12.

In other variants, the indicator component is different from the sealing agent and from a thread, for example a ball or a pellet integrated into the stopper.

In other variants, the change in color of the indicator component 15 is brought about on contact with a liquid other than water, for example a product contained in a diluent or a semen preservative for animal semen.

In other variants, the material of the tube such as 11 is not transparent, but translucent, for example slightly colored; and the detection takes into account the passage of the light emitted by the indicator component through the material of the tube such as 11.

In other variants, the material of the tube 11 is opaque and the indicator component is excited for example with infrared light or ultraviolet light.

In other variants, the indicator component enables recognition of whether the current straw is an ordinary straw or a straw provided to be discriminated, is independent from the filling of the straw, that is to say that it emits light in the same manner whether the straw is in the empty state or in the full state. In these variants, the indicator component may form part of or not form part of the stopper of the straw. For example, when the indicator component does not form part of the stopper of the straw, it is a fluorophore agent present on a support associated externally of the tube 11, or even a fluorophore agent integrated into the material of the tube 11.

Numerous other variants are possible according to circumstances, and in this connection it is to be noted that the invention is not limited to the examples described and shown.

The invention claimed is:

1. A set comprising:
a straw for the preservation of a predetermined dose of liquid-based substance, comprising a tube, a gas-permeable liquid-tight stopper, which stopper is disposed in the tube in the neighborhood of one end, which tube and which stopper are configured for the stopper to be able to slide in the tube towards another end, and an indicator component configured to emit, at least when the straw is in the filled state, light of which the spectrum comprises at least one peak each having a respective crest of predetermined wavelength; and
a detector for recognition of said straw, wherein said detector is configured for detecting absence or presence of said at least one peak in the light spectrum emitted by said indicator component;
said detector being part of a straw filler comprising a processor connected to said detector and configured to emit a stop signal for said straw filler in case said detector detects a straw in which there is absence of said at least one peak in said spectrum of the light emitted by said indicator component.

2. A set according to claim 1, wherein said indicator component is configured to emit light of which the spectrum comprises several said peaks of which the respective crests are of different wavelengths.

3. A set according to claim 1, wherein said indicator component is configured to emit light of which the spectrum comprises said at least one peak in response to illumination by light comprising a predetermined range of wavelengths that is offset relative to the predetermined wavelength of said respective crest of each of said at least one peak.

4. A set according to claim 1, wherein said indicator component forms part of said stopper and is configured to emit light comprising said at least one peak when said indicator component has been in contact with said substance and does not comprise said at least one peak, in the absence of prior contact with said substance.

5. A set according to claim 4, wherein said stopper is formed by two plugs made from a fibrous substance enclosing a powder transforming on contact with said substance into an impermeable paste or gel adhering to the wall of the tube so that the stopper is liquid-tight, said indicator component comprising said powder.

6. A set according to claim 5, wherein said powder comprises a powder of a salt that is non-fluorophore in a dry state and fluorophore when it is dissolved in water.

7. A set according to claim 6, wherein said salt forms part of the group comprising a fluorescein salt, a Rhodamine B salt, a Rhodamine 6G salt and a salt which has the following formula:

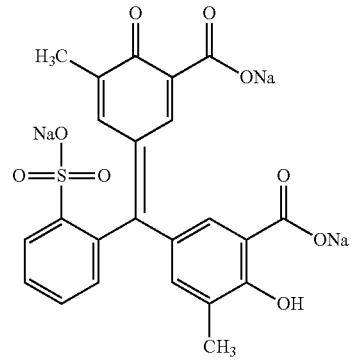

and which is identified by the number CAS 64-18-9.

8. A set according to claim 6, wherein said powder comprises between 1/100 and 1/100000 by weight of said salt powder.

9. A set according to claim 6, wherein said powder is formed by said salt powder and by powder of material that polymerizes on contact with water.

10. A set according to claim 9, wherein said powder of material that polymerizes on contact with water is alginate.

11. A set according to claim 1, wherein said indicator component comprises an indicator thread configured to emit said light of which the spectrum comprises said at least one peak.

12. A set according to claim 11, wherein said stopper is formed by two plugs made from a braided fibrous substance enclosing a powder which, on contact with a liquid, transforms into an impermeable paste or gel adhering to the wall of the tube so that the stopper is liquid-tight, at least one of the two plugs comprising said indicator thread.

13. A set according to claim 1, wherein said indicator component of the stopper of the straw is configured to emit light of which the spectrum comprises said at least one peak in response to illumination by light comprising a predetermined range of wavelengths that is offset relative to the predetermined wavelength of said respective crest; and said set further comprises an illuminator to illuminate said indicator component by light comprising said predetermined range of wavelengths.

14. A set according to claim 1, wherein the at least one peak comprises more than one peak and the detector is configured to detect the absence or the presence of each said more than one peak.

* * * * *